United States Patent [19]

Mesens et al.

[11] Patent Number: 5,674,871
[45] Date of Patent: Oct. 7, 1997

[54] IONTOPHORETIC DELIVERY OF AN ANTIMIGRAINE DRUG

[75] Inventors: Jean Louis Mesens, Wechelderzande; Gustaaf Van Reet, Kasterlee; Frank Maria Jozef De Beukelaar, Beerse, all of Belgium

[73] Assignee: Janssen Pharmaceutica N. V., Beerse, Belgium

[21] Appl. No.: 586,700

[22] PCT Filed: Aug. 19, 1994

[86] PCT No.: PCT/EP94/02764

§ 371 Date: Jan. 26, 1996

§ 102(e) Date: Jan. 26, 1996

[87] PCT Pub. No.: WO95/05815

PCT Pub. Date: Mar. 2, 1995

[30] Foreign Application Priority Data

Aug. 27, 1993 [EP] European Pat. Off. ............. 93202523

[51] Int. Cl.⁶ .......................... A61K 31/505; A61K 31/35; A61K 31/445; A61K 31/415; A61K 31/40
[52] U.S. Cl. .......................... 514/275; 514/456; 514/320; 514/397; 514/385; 514/422
[58] Field of Search ..................... 514/275, 456, 514/320, 397, 385, 422

[56] References Cited

U.S. PATENT DOCUMENTS 5,541,180 7/1996 Van Lommen et al. ............. 514/218

FOREIGN PATENT DOCUMENTS

WO91/15260 10/1991 WIPO.
WO A 93/17017 9/1993 WIPO.

OTHER PUBLICATIONS

Lambert et al., "The Spinal Cord Processing of Input from the Superior Sagittal Sinus; Pathway and Modulation by Ergot Alkaloids", Brain Research, vol. 597, No. 2, 1992, pp. 321–330.

Primary Examiner—William R.A. Jarvis
Attorney, Agent, or Firm—Charles J. Metz

[57] ABSTRACT

The present invention relates to the iontophoretic delivery to a patient, more in particular to a migraine patient, of a compound of formula (I) as shown hereinunder. The invention also relates to a device for the iontophoretic delivery of a compound of formula (I), as well as to a composition containing a compound of formula (I), which can be applied in a device for iontophoretic delivery. Said compounds are benzopyranalkylaminoalkyl substituted guanidines having the formula

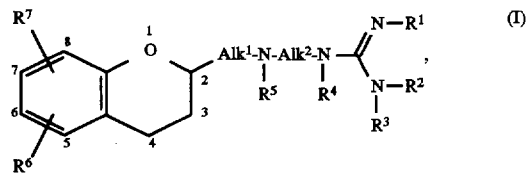

the pharmaceutically acceptable acid addition salts thereof, and the stereochemically isomeric forms thereof, wherein $R^1$ is hydrogen or $C_{1-6}$alkyl; $R^2$ is hydrogen, $C_{1-6}$alkyl, $C_{3-6}$alkenyl or $C_{3-6}$alkynyl; $R^3$ is hydrogen or $C_{1-6}$alkyl; or $R^2$ and $R^3$ taken together form a bivalent radical of formula $-(CH_2)_m-$ wherein m is 4 or 5; or $R^1$ and $R^2$ taken together form a bivalent radical of formula $-CH=CH-$ or of formula $-(CH_2)_n-$, wherein n is 2, 3 or 4; or $R^3$ may represent a bond when $R^1$ and $R^2$ taken together form a bivalent radical of formula $-CH=CH-CH=$; $R^4$ and $R^5$ each independently are hydrogen or $C_{1-6}$alkyl; $Alk^1$ is a bivalent $C_{1-3}$alkanediyl radical; $Alk^2$ is a bivalent $C_{2-15}$alkanediyl radical; and $R^6$ and $R^7$ each independently are hydrogen, halo, $C_{1-6}$alkyl, $C_{3-6}$alkenyl, $C_{3-6}$alkynyl, hydroxy, $C_{1-6}$alkyloxy or cyano.

24 Claims, No Drawings

IONTOPHORETIC DELIVERY OF AN ANTIMIGRAINE DRUG

CROSS-REFERENCE TO RELATED APPLICATIONS

This application is based upon PCT Application Serial No. PCT/EP 94/02764, filed Aug. 19, 1994, which claims priority from European Patent Application Serial No. 93.202.523.2, filed on Aug. 27, 1993.

The present invention relates to the iontophoretic delivery to a patient, more in particular to a migraine patient, of a compound of formula (I) as shown hereinunder. The invention also relates to a device for the iontophoretic delivery of a compound of formula (I), as well as to a composition comprising a compound of formula (I), which can be applied in a device for iontophoretic delivery.

Although in general, oral administration of a drug is considered as most convenient, this route poses particular problems when administering a drug, more in particular an anti-migraine drug, to patients suffering from a migraine attack. Migraine patients often feel nauseous, sometimes resulting in violent vomiting, thus hampering the oral administration of the anti-migraine drug. The successful oral delivery of some anti-migraine substances is also impeded by its susceptibility to degradation by the acid environment of the stomach and by the digestive activity of several enzymes in the gastrointestinal tract. Other disadvantages of the oral route are the often poor absorption due to gastroparesis and the extensive first-pass elimination in the liver (the hepatic first-pass effect), whereby a compound is transformed in the liver into a metabolite more prone for excretion. Along with convenient administration, it is essential for an effective treatment of a migraine attack that the activity of the drug sets on immediately, or at least very rapidly, after administration and that the effect lasts long enough. Hence a means of directly inserting the drug into the bloodstream should be a method of choice for the administration of an anti-migraine drug. An obvious way of doing so is by injecting a solution of the drug either intravenously or subcutaneously. However, the consequent pain, risk of infection, the complex procedures of self-administration and potential for low patient compliance make such parenteral administration undesirable.

Transdermal delivery is an attractive alternative because: (a) it avoids gastrointestinal degradation and the hepatic first-pass effect; (b) it lends itself to a controlled and/or sustained release; (c) it allows for convenient and simple self-administration and encourages patient compliance, since a transdermal formulation would be easy to apply or to remove.

Traditional transdermal drug delivery systems are based on the transport of drugs into the skin by diffusion through the outermost layer of the epidermis, i.e. the stratum corneum. The number of solutes which can be delivered by this route are limited due to the excellent barrier properties of the said stratum corneum. Hence, attainment of a therapeutically effective level is therefore difficult without some form of facilitation. One means of facilitation is the delivery of the drug by electrokinetic action, more in particular by iontophoretic action. The principle of iontophoresis is that ionized (or polar) drug molecules can be driven into the skin if an appropriate electrical potential is applied across the skin. Iontophoresis may be due solely to electromigration, i.e. the movement of ionized drug molecules across an electrical field per se, or it may be due to a combined effect of electromigration and electroosmosis. The latter is a transdermal flux of liquid solvent containing the drug by the presence of an electrical field.

The problem to be solved is to find or develop compounds and compositions, which have the desired anti-migraine activity and which are susceptible for said convenient iontophoretic delivery.

Recently, it was discovered that the compounds of formula (I) show $5HT_{1-like}$ agonistic activity and, more in particular, anti-migraine activity. Unexpectedly it has been found that these compounds of formula (I) can be delivered via iontophoretic action. Said compounds are dihydrobenzopyranalkylaminoalkyl substituted guanidines having the formula

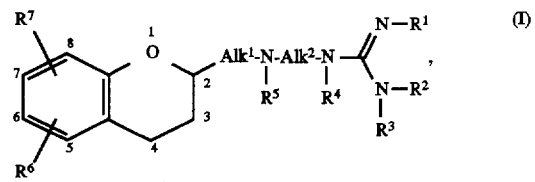

the pharmaceutically acceptable acid addition salts thereof, and the stereochemically isomeric forms thereof, wherein $R^1$ is hydrogen or $C_{1-6}$alkyl;
$R^2$ is hydrogen, $C_{1-6}$alkyl, $C_{3-6}$alkenyl or $C_{3-6}$alkynyl;
$R^3$ is hydrogen or $C_{1-6}$alkyl; or
$R^2$ and $R^3$ taken together form a bivalent radical of formula —$(CH_2)_m$- wherein m is 4 or 5; or
$R^1$ and $R^2$ taken together form a bivalent radical of formula —CH=CH— or of formula —$(CH_2)_n$-, wherein n is 2, 3 or 4; or
$R^3$ may represent a bond when $R^1$ and $R^2$ taken together form a bivalent radical of formula —CH=CH—CH=;
$R^4$ and $R^5$ each independently are hydrogen or $C_{1-6}$alkyl;
$Alk^1$ is a bivalent $C_{1-3}$alkanediyl radical;
$Alk^2$ is a bivalent $C_{2-15}$alkanediyl radical; and
$R^6$ and $R^7$ each independently are hydrogen, halo, $C_{1-6}$alkyl, $C_{3-6}$alkenyl, $C_{3-6}$alkynyl, hydroxy, $C_{1-6}$alkyloxy or cyano.

In the foregoing definitions, the term "halo" is generic to fluoro, chloro, bromo, iodo; the term "$C_{1-6}$alkyl" means straight or branched saturated hydrocarbon radicals having from 1 to 6 carbon atoms, such as, methyl, ethyl, propyl, butyl, pentyl, hexyl, and the like; "$C_{3-6}$alkenyl" defines straight and branch chained hydrocarbon radicals containing one double bond and having from 3 to 6 carbon atoms, such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated, "$C_{3-6}$alkynyl" defines straight and branch chained hydrocarbon radicals containing one triple bond and having from 3 to 6 carbon atoms, such as, for example, 2-propynyl, 3-butynyl, 2-butynyl, 2-pentynyl, 3-pentynyl, 3-hexynyl, and the like; and the carbon atom of said $C_{3-6}$alkynylradical being connected to a nitrogen atom preferably is saturated; "$C_{1-3}$alkanediyl" is meant to comprise straight or branched saturated hydrocarbon radicals containing 1 to 3 carbon atoms, such as, methylene,ethanediyl, propanediyl, and the like; "$C_{2-15}$alkanediyl" is meant to comprise straight or branched saturated hydrocarbon radicals having from 2 to 15 carbon atoms, such as, ethanediyl, propanediyl, butanediyl, pentanediyl, hexanediyl, heptanediyl, octanediyl, nonanediyl, decanediyl, undecanediyl, dodecanediyl, tridecanediyl, tetradecanediyl, pentadecanediyl and the branched isomers thereof.

Pharmaceutically acceptable acid addition salts as mentioned hereinabove comprise the therapeutically active nontoxic acid addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term "stereochemically isomeric forms" as used hereinbefore and hereinafter defines all the possible isomeric forms which the compounds of formula (I) may possess. Unless otherwise mentioned or indicated, the chemical designation of compounds denotes the mixture Of all possible stereochemically isomeric forms, said mixtures containing all diastereomers and enantiomers of the basic molecular structure. More in particular, stereogenic centers may have the R- or S-configuration. The present invention clearly intends to embrace in its scope both the individual stereochemically isomeric forms and the mixtures thereof.

It has to be understood that, when mixtures of enantiomers are present, they may be separated according to classical resolution methods, e.g. by fractional crystallization of their acid addition salts with a suitable chiral acid or by the separation by chromatography using a chiral phase.

Moreover, some of the compounds of formula (I) may also exist in their tautomeric forms. Such forms although not explicitly indicated in the above formula (I) are intended to be included within the scope of the present invention.

$R^1$ is suitably hydrogen or methyl;
$R^2$ is suitably hydrogen or methyl;
$R^3$ is suitably hydrogen or methyl;
preferably $R^1$ and $R^2$ are taken together to form a bivalent radical of formula —CH=CH—, —(CH$_2$)$_2$- or —(CH$_2$)$_3$-; or when $R^3$ is a free bond $R^1$ and $R^2$ taken together form a bivalent radical or formula —CH=CH—CH=;
$R^4$ is suitably methyl or hydrogen, preferably hydrogen;
$R^5$ is suitably methyl or hydrogen, preferably hydrogen;
$R^6$ and $R^7$ suitably are hydrogen, halo, or $C_{1-6}$alkyl, preferably hydrogen, fluoro, methyl or ethyl.

Interesting compounds of formula (I) are those compounds of formula (I) wherein Alk$^1$ is $C_{1-2}$alkanediyl, especially methylene.

Other interesting compounds are those compounds of formula (I) wherein Alk$^2$ is $C_{2-6}$alkanediyl, particularly, ethanediyl, propanediyl, butanediyl, pentanediyl, hexanediyl, preferably 1,3-propanediyl.

Most preferred compounds are N-[(3,4-dihydro-2H-1-benzopyran-2-yl)methyl]-N'-(1,4,5,6-tetrahydro-2-pyrimidinyl)-1,3-propanediamine, the stereochemical isomers thereof, particularly the R-isomer, and the pharmaceutically acceptable acid addition salts thereof.

The compounds of formula (I) may be prepared following art-known procedures.

The process of iontophoretic drug delivery is performed in general by putting a composition comprising the drug onto intact skin. This composition may for instance be a solution (absorbed onto some porous material, for instance a piece of filter paper or a piece of hydrophilic polyurethane) or a gel. The composition is then covered by an electrode. A second electrode is placed elsewhere on the skin, and a direct current source is connected between the electrodes in such a way that the electrode in contact with the drug solution assumes the same charge as the ionized drug. Under influence of the electric field present, drug molecules migrate through the skin. A current flows between the electrodes, part of which is carded by the drug.

Iontophoretic devices as such are known in the art, for instance from, WO-A 9116946, WO-A 9116944, WO-A 9116943, WO-A 9115261, WO-A 9115260, WO-A 9115259, WO-A 9115258, WO-A 9115257, WO-A 9115250, WO-A 9109645, WO-A 9108795, WO-A 9004433, WO-A 9004432, WO-A 9003825, EP-A 254965, U.S. Pat. No. 4,717,378, EP-A 252732 and GB-A 2239803.

As a first aspect of this invention an iontophoretic drug delivery system for administering a compound of formula (I) is provided. Basically, said iontophoretic drug delivery system, also called an electrotransdermal drug delivery system (ETS), is a device containing four components: a power source, e.g. batteries; control circuitry; electrodes; and reservoirs. The device itself may be a one-part or a two-part device; in the latter case a first part may contain the control circuitry and an associated power source, while the second part may consist of an electrode unit containing the above-mentioned active ingredient. The housing of the device or of the parts of the device are usually moldings normally made of electrically nonconductive material, such as hydrophobic non-conducting polymeric materials, e.g. polyethylene or polypropylene. The opening at the base of the molding, which is in contact with the skin may optionally be covered by a microporous membrane which is attached to the bottom of the molding and is preferably made of electrically nonconductive material, such as stretched polyethylene or polypropylene film. The membrane can be coated with a surfactant if necessary for the purpose of wettability. The microporous membrane allows electrical migration of ions but inhibits leakage of fluid. The material of which the microporous membrane is made can vary with the actual active ingredient used in the device.

The electrode system consists of an anode, a cathode, and two reservoirs, one containing drug ions and the other containing, for instance, a biocompatible salt, such as sodium chloride, alkaline suits of inorganic acids, e.g. chlorides, sulfates, nitrates, carbonates, phosphates, or of organic acids, e.g. ascorbates, citrates, acetates. Delivery of a positive drug salt, as is the case here, requires that the drug salt be placed during actual delivery in the anode reservoir, while delivery of a negative drug requires placement of the drug salt in the cathode reservoir. Delivery of the same drug out of both reservoirs in an alternating fashion can also be accomplished by periodically reversing the polarity of the electrodes.

Electrodes may be metal foils, polymer matrix loaded with metal powder, powdered graphite, carbon fibers or other suitable electrically conductive material. Suitable metals for use in electrodes are for instance platinum, silver, aluminium, copper, lead, iron, tin, chromium or zinc. Also metal/insoluble salt electrodes may be used, such as silver/silverhalide electrodes, particularly silver/silverchloride electrodes. Interesting electrodes are platinum electrodes. Preferably silver/silverchloride electrodes are used.

The configuration of electrodes can be very simple or may comprise a plurality of spaced-apart and isolated electrodes arranged on a first surface adapted for contact with the skin. The arrangement of electrodes can be alligned, for instance, side-by-side or concentrically. The concentric allignment of the electrodes can be circular, elliptical, rectangular or any of a variety of geometric configurations. Said arrangement of a plurality of electrodes may facilitate delivery of the active ingredient by minimizing current requirements for such delivery as well as minimizing any skin irritation that might be associated with the use of the device.

The combined skin contacting areas of electrode assemblies can vary from less than 1 cm$^2$ to greater than 200 cm$^2$. The average device will have a contacting area from about 5 cm$^2$ to about 50 cm$^2$.

The power source can be batteries or a galvanic couple. Preferred power sources are batteries. Batteries to be used in these drug delivery systems will usually be the conventional miniature or "light-weight" batteries. For example, conventional sheet batteries and microbatteries may be used. Suitable batteries are alkaline batteries and lithium batteries of the type used in hearing aids and watches.

The iontophoretic system further consists of an electronic control module including an ON/OFF switch. The control circuitry of the iontophoretic system can be as simple as a resistor, which would limit the applied current to some maximum value, or as complex as an integrated circuit, which would allow for time varying or feedback-controlled drug delivery. In this manner the iontophoretic delivery system may for instance reduce the chance of under- or overdosing as a result of said possibility to preprogram the drug delivery at the required therapeutic rate. An interesting preprogrammed delivery scheme in this case of administering an anti-migraine drug may be: first the administration of a bolus of the compound of formula (I) to alleviate the instant pain immediately and after some time a sustained delivery of smaller mounts of the compound to avoid the possibility of break-through head-aches.

The device may also include an electrical circuit with means for indicating that an active ingredient is being actively delivered. This feature is desirable for example to reassure the patient that he or she is receiving medication.

Compositions suitable for introducing in a iontophoretic device comprising a compound of formula (I) provide a further aspect of this invention. Said compositions may for instance be a in a liquid form contained in a reservoir having a membrane which is permeable for active ingredient.

Alternatively, the active ingredient may be dispersed in a matrix of a solid, semi-solid or mucilaginous material and optionally having an active ingredient permeable membrane associated therewith. The matrix material is suitably a hydrogel, polyurethane, silicone or other material known in the art for holding a drug in a stable condition prior to release to the skin. The drug may also be contained in the reservoir using an ion-exchange resin or a ligand affinity medium as the drug reservoir matrix.

Suitable materials for forming a matrix for use in an electrode for the device according to the invention include, for example, plant extracts, vegetable oils, gums, synthetic or natural polysaccharides, polypeptides, alginates, hydrocarbons, synthetic polymers, mineral and silicon compounds and mixtures thereof. Such materials are solidifying or gel-forming agents which upon mixing and/or heating with the active ingredient and optionally one or more auxiliary material(s) in a solvent or a mixture of solvents form a matrix with the active ingredient and auxiliary material(s), if present, dispersed therethrough.

The term "solidifying agent" as used herein also embraces thickening, hardening, setting, suspending or the like agents.

Suitable plant extracts include agar-agar, ispaghula, psyllium, cydonia and ceratonia or a mixture thereof. A suitable vegetable oil is hydrogenated castor oil. Examples of suitable gums include guar gum, acacia gum, ghatti gum, karaya gum and tragacanth gum or a mixture thereof. Suitable synthetic and natural polysaccharides include alkylcelluloses, hydroxyalkylcelluloses, cellulose ethers, cellulose esters, nitro celluloses dextrin, carrageenan, pectin, furcellaran and starch or starch derivatives. An example of a preferred starch derivative is sodium starch glycolate. Synthetic polymers include polyvinylalcohol, polyacrylamide, polyacrylic acid, polyvinylpyrrolidone, hydroxyethylmethylacrylate, polyethyleneoxides, polyethylene, polypropylene, polyisoprenes, polyisobutylene, polyvinylacetate. Suitable polypeptides include zein, gelatin, collagen and polygeline or mixtures thereof. Suitable alginates include alginic acid, propylene glycol alginate and sodium alginate or a mixture thereof.

Preferred hydrocarbons include soft paraffin and hard paraffin, especially white petrolatum. Especially preferred synthetic polymers are carbovinyl polymer or polyurethane.

Suitable minerals include bentonite, hectorite, aluminium magnesium silicate and magnesium silicate or a mixture thereof.

Suitable compounds based on silicon include colloidal silicon dioxide, silicones, polysiloxanes and silica gels or a mixture thereof.

In the case of a hydrogel the solvent used is preferably water. The solvent used may suitably be an alcohol such as ethanol or stearyl alcohol, glycerol, propylene glycol, polyethylene glycol or silicone or a mixture thereof, including mixtures with water.

Penetration enhancers may also be used. Such penetration enhancers are preferably neither toxic nor irritating nor allergenic. Suitable penetration enhancers are, for instance, ethanol and higher alcohols, N-decylmethylsulfoxide, polyethylene glycol monolaurate, dilaurate and related esters, glycerol monolaurate and related mono-, di- and trifunctional glycerides, diethyl toluamide, N,N-dimethyl lauramide, N,N-dimethyl lauramine oxide, sodium lauryl sulfate, sodium dodecylsarcosinate, cholesterol hemisuccinate, sodium cetyl sulfate, sodium dodecylbenzenesulfonate, sodium dioctylsulfosuccinate, and quaternary ammonium compounds, such as cetyl trimethylammonium chloride, and the like.

Suitable auxiliary materials may include one or more of the following: an antimicrobial agent, a preservative, a anti-oxidant, a plastizer, a tackifier, a surfactant, a humectant, a rheological agent, a local anaesthetic, a chelating agent, or a rubefacient.

The pH of the solution comprising the active ingredient may range from about 3 up to about 12. An even more interesting pH-range is between about 4 and about 11. Preferably the pH of the solution comprising the active ingredient is between about 8 and about 10. Most preferred pH-value is from about 8.5 to 9.5. Any buffer system capable of sustaining a pH as mentioned hereinabove can be used. Interesting examples are buffers on the basis of phosphoric acid, boric acid, citric acid, ethanolamine, tris (hydroxymethyl)-aminomethane, sodium bicarbonate, and the like or mixtures thereof. These buffer solutions can be prepared in an art-known manner. The choice of buffer solution is dependent upon the electrodes used and upon the other components of the composition comprising the compound of formula (I). For instance in the case where the electrodes used are silver/silverchloride electrodes, the buffer solution preferably contains chloride ions.

The ionic strength of the solution may range from about 0.001M to about 1M, particularly the range is between about 0.01M and about 0.5M, especially between about 0.05M and about 0.1M.

The amount of active ingredient in the ionized form in solution ranges preferably from about 0.1 mg/ml to about 100 mg/ml, preferably between about 1 mg/ml and about 50 mg/ml, especially between about 2 mg/ml and about 8 mg/ml.

The reservoir in contact with the counter electrode comprises a solution comprising a biocompatible salt. Suitable salts include sodium chloride or alkali metal salts and alkaline earth metal salts such as chlorides, sulfates, nitrates, carbonates, phosphates, and organic salts such as ascorbates, citrates, acetates and mixtures thereof.

The current density used can be in the region of 0.01–10 mA per $cm^2$. For example, the device most usually will operate at about 0.1 to about 0.7 mA per $cm^2$, preferably at about 0.2 to about 0.4 mA per $cm^2$. The current may be constant, variable or pulsed according to a given program of active ingredient delivery. Preferably the applied current is constant.

The device and composition according to the invention and as described hereinabove may be used in a method of delivering a compound of formula (I) by the iontophoretic route, which comprises applying said device to a patient. In practice, a patient suffering from a migraine attack would apply the iontophoretic delivery device somewhere on the body, for instance, on the arm or on the chest and switch on the device. When suffering from a recurrent headache, the patient can, at his option, again turn on the device and receive another dose of the antimigraine drug.

The iontophoretic delivery can be sustained for an uninterrupted period of time. It may be appropriate to intersperse a period of active iontophoretic delivery (i.e. a period wherein the iontophoretic device is turned on) with current-free intervals. An uninterrupted application period ranges from about 5 minutes up to about 120 minutes, particularly from about 10 to about 60 minutes, especially from about 15 to about 40 minutes. Current-free intervals may vary from about 5 minutes to 3 hours, particularly from about 15 minutes to about 2 hours, especially from about 30 minutes to 1 hour.

Experimental part
In vitro experiments

In the following examples a two chamber polycarbonate cell was used. The two compartments were separated from each other by a horizontally fixed piece (3 $cm^2$) of freshly excised full thickness abdominal skin of hairless rats. The donor compartment contained 1.4 ml of a solution of the test compound, i.e. R-N-[(3,4-dihydro-2H-1-benzopyran-2-yl) methyl]-N'-(1,4,5,6-tetrahydro-2-pyrimidinyl)-1,3-propanediamine (hereinafter referred to as "test compound"), spiked with $^3$H-labelled compound. The radiolabelled spike was introduced at a concentration of 1 μCi/ml. The receptor compartment was filled with a phosphate buffer (0.024M) at a pH of 7.4 isotonized with glucose. In both compartments electrodes were fixed, connected with each other via a power supply. The concentration of test compound migrated through the skin was measured at set points in time. Said concentration was determined by measuring the radioactivity in a liquid scintillation counter. The ratio of cumulated quantities detected in the receptor compartment to the skin area (3 $cm^2$) are shown as a function of time hereinunder. The results are expressed as mean value of at least three experiments. The standard error (SE) of the mean is also given.

EXAMPLE 1

The test compound was introduced into to the donor compartment at a concentration of 5 mg/ml in a borate buffer (0.1M) at a pH of 9.5. Platinum electrodes were fixed in both compartments. The applied conditions are enumerated hereinunder and the results are shown in Table 1.

No current was applied (column A).

A direct current of 0.2 $mA/cm^2$ for 1 hour was applied (column B).

A direct current of 0.4 $mA/cm^2$ for 1 hour was applied (column C).

A pulsed current (2 kHz) at a mean current density of 0.4 $mA/cm^2$ for 1 hour was applied (column D).

TABLE 1

| time hours | A μg/cm² ± SE | B μg/cm² ± SE | C μg/cm² ± SE | D μg/cm² ± SE |
|---|---|---|---|---|
| 0.25 | 0.33 ± 0.12 | 0.86 ± 0.15 | 1.11 ± 0.16 | 1.25 ± 0 |
| 0.50 | 0.57 ± 0.18 | 1.26 ± 0.24 | 4.55 ± 1.35 | 1.16 ± 0.02 |
| 0.75 | 0.90 ± 0.21 | 2.98 ± 0.84 | 13.80 ± 2.35 | 2.54 ± 0.63 |
| 1.00 | 0.69 ± 0.15 | 6.73 ± 1.23 | 33.25 ± 4.57 | 8.68 ± 1.15 |
| 1.25 | 0.61 ± 0.15 | 11.49 ± 2.34 | 49.51 ± 7.36 | 15.42 ± 3.19 |
| 1.50 | 0.71 ± 0.14 | 19.05 ± 3.09 | 55.24 ± 8.32 | 20.68 ± 6.13 |
| 1.75 | 0.79 ± 0.14 | 21.85 ± 0.69 | 61.00 ± 9.16 | 25.89 ± 5.55 |
| 2.00 | 0.81 ± 0.16 | 23.68 ± 2.28 | 72.05 ± 10.40 | 27.00 ± 3.73 |
| 2.25 | 0.88 ± 0.14 | 26.46 ± 2.38 | 80.92 ± 8.59 | 32.44 ± 5.46 |
| 2.50 | 0.93 ± 0.13 | 26.79 ± 2.49 | 82.59 ± 9.95 | 34.68 ± 6.93 |
| 3.00 | 1.04 ± 0.12 | 38.11 ± 1.36 | 94.31 ± 10.78 | 46.53 ± 6.83 |
| 3.50 | 1.11 ± 0.12 | 43.51 ± 0.59 | 111.84 ± 10.23 | 60.82 ± 10.99 |
| 4.00 | 1.34 ± 0.14 | 43.42 ± 2.60 | 116.57 ± 12.40 | 68.26 ± 10.97 |
| 4.50 | 1.51 ± 0.06 | 47.52 ± 1.52 | 123.37 ± 10.60 | 82.70 ± 10.43 |
| 5.00 | 1.61 ± 0.06 | 51.64 ± 2.02 | 127.08 ± 11.26 | 92.43 ± 11.73 |
| 5.50 | 1.84 ± 0.07 | 51.40 ± 2.41 | 133.91 ± 10.57 | 95.32 ± 13.09 |
| 6.00 | 2.04 ± 1.02 | 53.70 ± 4.43 | 138.01 ± 10.73 | 103.17 ± 15.01 |

EXAMPLE 2

The test compound was introduced in the donor compartment at different concentrations in different buffersystems at a pH of 9.5. Silver/silverchloride electrodes were fixed in both compartments. A direct current of 0.4 $mA/cm^2$ was applied for one hour. The applied conditions are enumerated hereinunder and the results are shown in Table 2.

The concentration of test compound was 5 mg/ml in a borate buffer (0.05M) containing 0.007M NaCl (column A).

The concentration of test compound was 7.5 mg/ml in a borate buffer (0.05M) containing 0.007M NaCl (column B).

The concentration of test compound was 5 mg/ml in a ethanolamine buffer (0.05M) (column C).

TABLE 2

| time hours | A μg/cm² ± SE | B μg/cm² ± SE | C μg/cm² ± SE |
|---|---|---|---|
| 0.25 | 1.29 ± 0.30 | 2.98 ± 0.81 | 3.17 ± 1.03 |
| 0.50 | 8.31 ± 2.45 | 12.38 ± 0.70 | 11.10 ± 2.47 |
| 0.75 | 18.81 ± 5.19 | 51.20 ± 6.11 | 24.72 ± 8.88 |
| 1.00 | 37.05 ± 7.65 | 114.45 ± 18.22 | 60.56 ± 13.42 |
| 1.25 | 46.34 ± 7.34 | 147.37 ± 29.35 | 66.10 ± 12.33 |
| 1.50 | 52.51 ± 10.05 | 161.45 ± 31.62 | 82.68 ± 17.35 |
| 1.75 | 62.34 ± 9.85 | 182.51 ± 30.67 | 92.20 ± 20.09 |
| 2.00 | 71.14 ± 12.69 | 208.34 ± 19.51 | 115.33 ± 21.78 |
| 2.25 | 75.08 ± 12.42 | 210.67 ± 15.28 | 134.62 ± 25.45 |
| 2.50 | 77.19 ± 15.06 | 218.98 ± 20.50 | 134.45 ± 22.18 |
| 3.00 | 92.62 ± 15.73 | 243.14 ± 19.18 | 150.19 ± 27.45 |
| 3.50 | 103.36 ± 10.69 | 265.94 ± 22.28 | 162.34 ± 25.82 |
| 4.00 | 115.79 ± 12.94 | 273.98 ± 15.67 | 174.49 ± 27.08 |
| 4.50 | 116.98 ± 13.00 | 282.86 ± 20.71 | 169.37 ± 16.09 |
| 5.00 | 133.51 ± 17.40 | 296.20 ± 15.74 | 177.54 ± 29.06 |
| 5.50 | 138.65 ± 18.82 | 306.37 ± 17.36 | 196.72 ± 25.43 |
| 6.00 | 139.13 ± 16.47 | 320.23 ± 19.05 | 200.30 ± 31.93 |

EXAMPLE 3

The test compound was introduced in the donor compartment at different concentrations in different buffersystems.

Platinum electrodes were fixed in both compartments. A direct current of 0.4 mA/cm² was applied for one hour. The applied conditions are enumerated hereinunder and the results are shown in Table 3.

The concentration of test compound was 5 mg/ml in a citrate buffer (0.05M) at a pH of 5.5 (column A).

The concentration of test compound was 5 mg/ml in a citrate buffer (0.1M) at a pH of 5.5 (column B).

TABLE 3

| time hours | A µg/cm² ± SE | B µg/cm² ± SE |
|---|---|---|
| 0.25 | 0 ± 0 | — |
| 0.50 | 1.81 ± 0.65 | 1.43 ± 0.33 |
| 0.75 | 4.76 ± 1.06 | 3.54 ± 0.70 |
| 1.00 | 13.71 ± 3.10 | 6.66 ± 1.72 |
| 1.25 | 15.18 ± 2.48 | 8.13 ± 2.73 |
| 1.50 | 19.34 ± 3.35 | 14.01 ± 5.35 |
| 1.75 | 20.01 ± 4.27 | 13.23 ± 3.91 |
| 2.00 | 20.25 ± 5.71 | 13,83 ± 3.53 |
| 2.25 | 25.65 ± 7.08 | 15.78 ± 3.74 |
| 2.50 | 26.92 ± 5.83 | 16.67 ± 3.54 |
| 3.00 | 33.15 ± 6.68 | 18.29 ± 3.29 |
| 3.50 | 40.31 ± 9.11 | 20.60 ± 3.06 |
| 4.00 | 41.97 ± 9.15 | 24.11 ± 5.02 |
| 4.50 | 48.63 ± 12.21 | 27.17 ± 4.09 |
| 5.00 | 46.54 ± 10.28 | 27.61 ± 4.55 |
| 5.50 | 52.98 ± 12.21 | 30.60 ± 4.03 |
| 6.00 | 53.28 ± 11.43 | 32.78 ± 5.30 |

In vivo experiment

EXAMPLE 4

Hydrophilic polyurethane 10 cm² foam patches (Allevyn, Smith & Nephew) were soaked with a solution of the test compound, i.e. R-N-[(3,4-dihydro-2H-1-benzopyran-2-yl)methyl]-N'-(1,4,5,6-tetrahydro-2-pyrimidinyl)-1,3-propanediamine (7.5 mg/ml of the test compound in ethanolamine buffer (0.05M) at a pH of 9.5). Ag/AgCl electrodes were inserted in the foam patch and connected to a direct current generator.

On the drug treatment day, volunteers were administered the test compound by an electrotransdermal drug delivery system (ETS) with a direct current of 0.2 mA/cm² applied for two consecutive 30 min periods (periods were separated by a current-free interval of 90 min). The drug delivery system (foam patch) was applied on the ventral side of the forearm of the volunteer and remained in place until 90 min after the second current application period (=240 min after start of 1 st current application).

Blood samples, blood pressure measurements and electrocardiogram recordings were performed at several time points during the ETS application period and at specific time points until 6 hours thereafter. The volunteers remained in the clinical pharmacology unit until 4 hours after start of the first current application period. To evaluate tolerability, the volunteers saw the investigator for a follow-up visit, which was scheduled between 1 and 7 days after drug administration.

Venous blood samples (5 ml) were taken from an anticubital vein (opposite to administration site) immediately before and at 30 (end of 1 st current application period), 60, 90, 120 (before 2nd current application period), 150 (end of 2nd current application period), 180, 210, 240, 300 and 360 min after start of the 1st current application period. The blood samples were collected in heparinized tubes.

Plasma concentrations of the test compound were determined by radio-immunoassay. Eight volunteers participated in the experiment and the mean value of the plasma concentration (in ng/ml) in the blood samples is given in Table 4.

TABLE 4

| Time hours | Mean plasma concentration (ng/ml) |
|---|---|
| 0 | ND |
| 0.5 | 4.49 |
| 1 | 1.02 |
| 1.5 | 0.61 |
| 2 | 0.33 |
| 2.5 | 5.37 |
| 3 | 1.76 |
| 3.5 | 1.18 |
| 4 | 1.11 |
| 6 | 0.50 |
| 24 | 0.21 |
| 72 | 0.24 |

ND: not detectable by the RIA-method (≦0.10 ng/ml)

We claim:

1. A iontophoretic drug delivery device characterized in that it comprises as an active ingredient a compound of formula

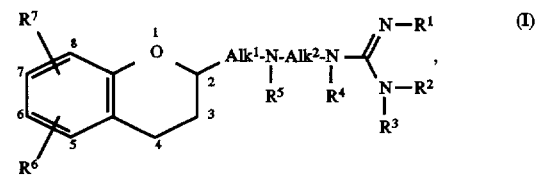

a pharmaceutically acceptable acid addition salt thereof, or a stereochemically isomeric form thereof, wherein
$R^1$ is hydrogen or $C_{1-6}$alkyl;
$R^2$ is hydrogen, $C_{1-6}$alkyl, $C_{3-6}$alkenyl or $C_{3-6}$alkynyl;
$R^3$ is hydrogen or $C_{1-6}$alkyl; or
$R^2$ and $R^3$ taken together form a bivalent radical of formula —$(CH_2)_m$— wherein m is 4 or 5; or
$R^1$ and $R^2$ taken together form a bivalent radical of formula —CH=CH— or of formula —$(CH_2)_n$—, wherein n is 2, 3 or 4; or
$R^3$ may represent a bond when $R^1$ and $R^2$ taken together form a bivalent radical of formula —CH=CH—CH=;
$R^4$ and $R^5$ each independently are hydrogen or $C_{1-6}$alkyl;
$Alk^1$ is a bivalent $C_{1-3}$alkanediyl radical;
$Alk^2$ is a bivalent $C_{2-15}$alkanediyl radical; and
$R^6$ and $R^7$ each independently are hydrogen, halo, $C_{1-6}$alkyl, $C_{3-6}$alkenyl,
$C_{3-6}$alkynyl, hydroxy, $C_{1-6}$alkyloxy or cyano.

2. A device according to claim 1 comprising as an active ingredient N-[(3,4-dihydro-2H-1-benzopyran-2-yl)methyl]-N'-(1,4,5,6-tetrahydro-2-pyrimidinyl)-1,3-propanediamine, a stereochemically isomeric form thereof or a pharmaceutically acceptable acid addition salt form thereof.

3. A device according to claim 1 or 2 wherein the active ingredient is in liquid form contained in a reservoir, having an active ingredient permeable membrane.

4. A device according to claim 1 or 2 wherein the active ingredient is dispersed in a matrix of a solid, semi-solid or mucilaginous material.

5. A device according to claim 4, wherein the matrix is comprised of a synthetic polymer.

6. A device according any of claims 1 or 2 wherein at least one of the electrodes is a silver/silver chloride electrode.

7. A device according to any of claims 1 or 2 including an electrode comprised of silver and a buffer containing chloride ions.

8. A device according to any of claims 1 or 2 wherein the device applies a level of electric current in the range of 0.01 to 10 mA/cm².

9. A device according to any of claims 1 or 2 wherein the device applies a level of current in the range of about 0.1 to 0.7 mA/cm².

10. A device according to any of claims 1 or 2 including a means for indicating that the active ingredient is being delivered.

11. A composition containing a compound of the formula:

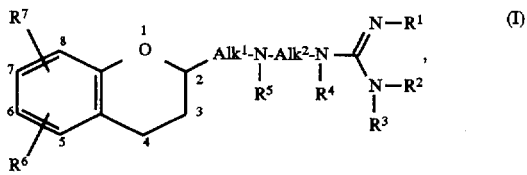

a pharmaceutically acceptable acid addition salt thereof, or a stereochemically isomeric form thereof, wherein:

$R^1$ is hydrogen or $C_{1-6}$alkyl;

$R^2$ is hydrogen, $C_{1-6}$alkyl, $C_{3-6}$alkenyl or $C_{3-6}$alkynyl;

$R^3$ is hydrogen or $C_{1-6}$alkyl;

or $R^2$ and $R^3$ taken together form a bivalent radical —$(CH_2)_m$- wherein m is 4 or 5;

$R^1$ and $R^2$ taken together form a bivalent radical of formula —CH—CH— or of formula —$(C_2)_n$- wherein n is 2, 3 or 4;

or $R^3$ may represent a bond when $R^1$ and $R^2$ taken together form a bivalent radical of formula —CH═CH—CH═;

$R^4$ and $R^5$ each independently are hydrogen or $C_{1-6}$alkyl;

$Alk^1$ is a bivalent $C_{1-3}$alkanediyl radical;

$Alk^2$ is a bivalent $C_{2-15}$alkanediyl radical; and $R^6$ and $R^7$ each independently are hydrogen, halo, $C_{1-6}$alkyl, $C_{3-6}$-alkenyl, $C_{3-6}$alkynyl, hydroxy, $C_{1-6}$alkyloxy or cyano, suitable for application in a iontophoretic drug delivery device.

12. The composition of claim 11 comprising said compound in an amount ranging from about 1 mg/mL to about 50 mg/mL.

13. A composition according to claims 11 or 12 wherein the composition has a pH ranging from 4 to 11.

14. A composition according to claim 11 or 12 wherein the composition has a pH ranging from about 8 to 10.

15. A composition according to claim 11 or 12 wherein the composition has a pH ranging from about 8.5 to 9.5.

16. A composition according to claim 11 or 12 including a buffering agent.

17. A composition according to claim 16 wherein the buffer comprises chloride ions.

18. A method for the treatment of migraine which comprises delivering to a patient by means of a iontophoretic device an effective amount of a compound of the formula:

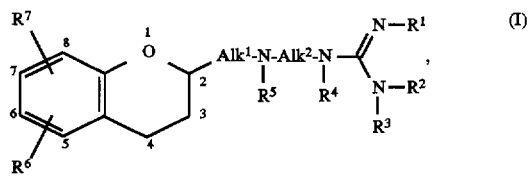

a pharmaceutically acceptable acid addition salt thereof, or a stereochemically isomeric form thereof, wherein:

$R^1$ is hydrogen or $C_{1-6}$alkyl;

$R^2$ is hydrogen, $C_{1-6}$alkyl, $C_{3-6}$alkenyl or $C_{3-6}$alkynyl;

$R^3$ is hydrogen or $C_{1-6}$alkyl;

or $R^2$ and $R^3$ taken together form a bivalent radical —$(CH_2)_m$- wherein m is 4 or 5;

or $R^1$ and $R^2$ taken together form a bivalent radical of formula —CH═CH— or of formula —$(CH_2)_n$- wherein n is 2, 3 or 4;

or $R^3$ may represent a bond when $R^1$ and $R^2$ taken together form a bivalent radical of formula —CH═CH—CH═;

$R^4$ and $R^5$ each independently are hydrogen or $C_{1-6}$alkyl;

$Alk^1$ is a bivalent $C_{1-3}$alkanediyl radical;

$Alk^2$ is a bivalent $C_{2-15}$alkanediyl radical; and $R^6$ and $R^7$ each independently are hydrogen, halo, $C_{1-6}$alkyl, $C_{3-6}$-alkenyl, $C_{3-6}$alkynyl, hydroxy, $C_{1-6}$alkyloxy or cyano.

19. Method according to claim 18 wherein the device administers the active ingredient at a bolus rate or amount and thereafter delivers the active ingredient at a rate or in an amount lesser than said bolus rate or amount, over a sustained period of time.

20. Method according to claim 18, wherein the device operates in a periodic manner characterized by periods of active iontophoretic delivery interspersed with substantially current-free intervals.

21. Method according to claim 20, wherein the periods of active iontophoretic delivery range from about 5 to 120 minutes.

22. Method according to claim 20, wherein the periods of active iontophoretic delivery range from about 10 to 60 minutes.

23. Method according to claim 20, wherein the substantially current-free intervals range from about 5 minutes to 3 hours.

24. Method according to claim 20, wherein the substantially current-free intervals range from about 15 minutes to 2 hours.

* * * * *